United States Patent

Gutman et al.

Patent Number: 6,093,820
Date of Patent: *Jul. 25, 2000

[54] METHOD AND REAGENTS FOR N-ALKYLATING UREIDES

[75] Inventors: Daniela Gutman, Rishon Lezion, Israel; Hershel Herzog, Tarytown, N.Y.

[73] Assignee: Taro Pharmaceutical Industries Ltd., Herzlia Pituach, Israel

[*] Notice: This patent issued on a continued prosecution application filed under 37 CFR 1.53(d), and is subject to the twenty year patent term provisions of 35 U.S.C. 154(a)(2).

[21] Appl. No.: 08/942,636

[22] Filed: Oct. 2, 1997

[51] Int. Cl.$^7$ ............... C07D 239/62; C07D 233/74; C07D 263/44; A61K 31/515

[52] U.S. Cl. ............ 544/302; 546/216; 546/242; 546/243; 548/317.1; 548/545; 548/547

[58] Field of Search ............ 544/302; 546/216, 546/242, 243; 548/317.1, 545, 547

[56] References Cited

U.S. PATENT DOCUMENTS 4,628,056  12/1986  Levitt et al. ............ 544/305

FOREIGN PATENT DOCUMENTS 2622981  8/1977  Germany.
4028040  12/1992  Germany.

OTHER PUBLICATIONS

Susumu Kamata, Nobuhiro Haga, Takeaki Matsui and Wataru Nagata, Studies of Antitumor–Active 5–Fluorouracil Derivatives. I. Synthesis of N–Phthalidyl 5–Fluorouracil Derivatives, Chemical And Pharmaceutical Bulletin, vol. 33, No. 8, 1985, pp. 3160–3175.

JP Gesson, JC Jacquesy, D. Rambaud, A practical method for N–alkylation of succinimide and glutarimide, Bulletin De La Societe Chimique De France, vol. 129, No. 3, 1992, pp. 227–231.

P. Casara et al., Synthesis of acid stable fluorinated acyl-nucleosides, vol. 32, No. 31, 1991, pp. 3823–3826.

Foye, "Principles of Medicinal Chemistry", 3rd ed., 1990, pp. 164, 179.

Karger et al., "Methoxymethyl Methanesulfonate, A Novel Active Oxyalkylating Agent", Journal of the American Chemical Society, 91:5663 (1969).

Aldrich Chemical Catalog, 1990–1991, p. 303.

Groth et al., EP–726252, (1996) (Abstract only).

Samour et al., DE1939787, (1970) (Abstract only).

*Primary Examiner*—Mukund J. Shah
*Assistant Examiner*—Bruck Kifle
*Attorney, Agent, or Firm*—Venable Attorneys; Michael A. Gollin

[57] ABSTRACT

A method of N-alkoxyalkylating ureides according to the invention comprises reacting a ureide of structure I

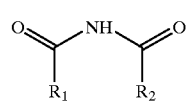

with an alkylating agent of structure III

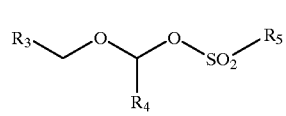

in the presence of a basic catalyst in an aprotic reaction medium. The ureide may be a 5,5-disubstituted barbituric acid, or it may be phenytoin, glutethimide, and ethosuximide. The alkylating agent is an ester of a sulfonic acid. The base may be a hydride or amine. A preferred process comprises N-alkoxyalkylating 5,5-diphenyl-barbituric acid with methoxymethyl methanesulfonate in the presence of di-isopropyl ethyl amine and isolating the resultant N,N'-bismethoxymethyl-5,5-diphenyl-barbituric acid. The invention also contemplates the novel compounds N-methoxymethyl-5,5-diphenylbarbituric acid, N-methoxymethyl ethosuximide, and N-methoxymethyl glutethimide, and a method comprising administering them to a patient.

26 Claims, No Drawings

METHOD AND REAGENTS FOR N-ALKYLATING UREIDES

BACKGROUND OF THE INVENTION

The invention relates to a new means for N-alkylating ureides that is higher yielding, more convenient, and safer to use than techniques practiced heretofore. This approach is particularly suited to preparing N-(alkoxyalkylene) ureides, which include anti-convulsant drugs of the N-substituted barbituric acid class.

The term ureide is used in e.g. Foye, *Principles of Medicinal Chemistry,* 3d ed. (1990), pp. 164, 179, which is incorporated herein by reference. Ureides are a class of imides of general structure I:

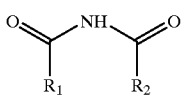

Examples include hypnotics, such as acecarbromal, apronalide, bromisolvalum, capuride, carbromal, and ectylurea; and anticonvulsant drugs such as hydantoins, glutarimides, oxazolidinediones, succinimides, and barbiturates such as barbituric acid (structure II).

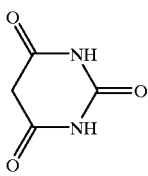

U.S. Pat. No. 4,628,056 teaches a method of making 1,3 bis(methoxymethyl)-5,5-diphenyl barbituric acid (also called N,N'-bis(methoxymethyl)-5,5-diphenyl barbituric acid) by dissolving diphenyl barbituric acid in cooled dimethylformamide, adding sodium hydride, then adding chloromethyl methyl ether. Chloromethyl methyl ether has been widely used to alkylate with a methoxymethylene function. However, it is highly toxic and regulated as a carcinogen. It is extremely volatile and flammable under exothermic reaction conditions, and alternatives to its use are strongly desirable.

Almost three decades ago, methoxymethyl methanesulfonate was identified as an agent for alkylating some alcohols and amines in a self-catalyzing reaction. Karger et al., J.A.C.S. 91:5663 (1969). With amines, the reaction was complex and led to salts, dimers, and other side products being formed. This method has not been applied to alkylation of ureides, or imides, for which there are major differences in electron availability at nitrogen.

SUMMARY OF THE INVENTION

The inventive method avoids the use of volatile, carcinogenic chloromethyl methyl ether, replacing that reagent with a more reactive, less volatile alternative which may be generated in situ (without risk to the operator).

The invention solves a previously unrecognized problem limiting the applicability of methoxymethanesulfonate alkylation to alcohols and amines. Ureides are much less basic than amines, so a different method for oxyalkylation is required. This invention differs from the method of Karger et al. by using a ureide, a non-aqueous basic catalyst, and an aprotic solvent, modifications which were not previously known or suggested. The inventive method allows use of a variety of sulfonates to prepare a broad variety of oxyalkylated ureides, some not previously known. The simplicity and convenience of the invention provide advantages that were not previously appreciated.

A method of N-alkoxyalkylating ureides according to the invention comprises reacting a ureide of structure I with an alkylating agent of structure III in the presence of a basic catalyst in an aprotic reaction medium. The alkylating agent III may be combined directly with the ureide, or the method may include reacting in situ a mixed anhydride of acetic acid and a sulfonic acid with a dialkoxymethane to provide the alkylating agent III. The method preferably involves isolating the resultant N-alkoxyalkylated ureide.

Preferably, the ureide is a 5,5-disubstituted barbituric acid, phenytoin, glutethimide, or ethosuximide. The alkylating agent may be methoxymethyl methanesulfonate, methoxymethyl benzenesulfonate, or methoxymethyl p-toluenesulfonate. The base may be selected from sodium hydride, triethyl amine, and di-isopropyl ethyl amine.

When the process includes the step of reacting a dialkoxymethane and a mixed acetic sulfonic anhydride to produce the resulting ester of the sulfonic acid, that reaction may be carried out in the same vessel as the following reaction with the ureide (done sequentially).

A preferred process comprises N-alkylating 5,5-diphenylbarbituric acid with a reagent selected from the group consisting of methoxymethyl methanesulfonate, methoxymethyl benezenesulfonate, and methoxymethyl p-toluenesulfonate, in the presence of di-isopropyl ethyl amine and isolating the resultant N,N'-bismethoxymethyl-5,5-diphenyl-barbituric acid.

The invention also contemplates the novel compounds N-methoxymethyl-5,5-diphenyl-barbituric acid, N-methoxymethyl ethosuximide and N-methoxymethyl glutethimide, methods of making them, and a method comprising administering to a patient an effective amount of a pharmaceutical agent selected from the group consisting of N-methoxymethyl-5,5-diphenyl-barbituric acid, N-methoxymethyl ethosuximide and N-methoxymethyl glutethimide.

Further objectives and advantages will become apparent from a consideration of the description and examples.

DETAILED DESCRIPTION OF THE PREFERRED EMBODIMENTS

In describing preferred embodiments of the present invention illustrated in the drawings, specific terminology is employed for the sake of clarity. However, the invention is not intended to be limited to the specific terminology so selected, and it is to be understood that each specific element includes all technical equivalents which operate in a similar manner to accomplish a similar purpose.

The reagent class which possesses the desirable N-alkylating properties is characterized as compounds of structure III

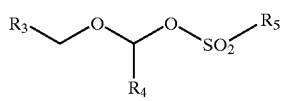

(III)

where the R groups are preferably as follows:

$R_3$=H, lower alkyl, phenyl, or substituted phenyl $R_4$=H, lower alkyl, phenyl, or substituted phenyl $R_5$=lower alkyl, phenyl, or substituted phenyl Particular examples of structures belonging to this class are listed in Table 1:

TABLE 1

| | Compound III | $R_3$ | $R_4$ | $R_5$ |
|---|---|---|---|---|
| 1. | methoxymethyl methanesulfonate | H | H | $CH_3$ |
| 2. | ethoxymethyl methanesulfonate | $CH_3$ | H | $CH_3$ |
| 3. | benzyloxymethyl methanesulfonate | phenyl | H | $CH_3$ |
| 4. | methoxymethyl ethanesulfonate | H | H | $C_2H_5$ |
| 5. | methoxymethyl benzenesulfonate | H | H | phenyl |
| 6. | methoxymethyl p-toluenesulfonate | H | H | tolyl |
| 7. | methoxylbenzylidene methanesulfonate | H | phenyl | $CH_3$ |
| 8. | methoxyethylidene methanesulfonate | H | $CH_3$ | $CH_3$ |

A particularly preferred reagent is methoxymethyl methanesulfonate.

The ureides which have been shown to be alkylated belong to the family of compounds having structure I:

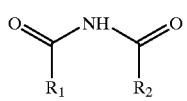

I which may be linear (with $R_1$ and $R_2$ being alkyl, aryl, or arylalkyl), or cyclic ($R_1$ and $R_2$ bonded to form a ring). Tables 2 and 3 (taken from Foye et al., Principles of Medicinal Chemistry, 3rd Edition (Lea and Febiger 1990), pp.164 and 179) depict ureide drugs.

TABLE 2

Structure of Anticonvulsant Drugs Containing the Ureide Structure

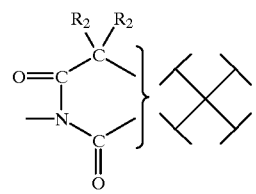

Ureide Structure

| Class of Compounds | |
|---|---|
| Barbiturates | 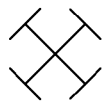 |
| Hydantoins | 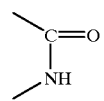 |
| Glutarimides | 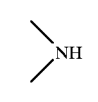 |
| Oxazolidinediones | 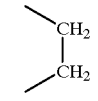 |
| Succinimides |  |

TABLE 3

Ureide Hypnotics

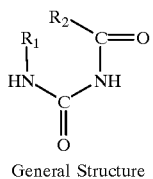

General Structure

| Generic Name | Chemical Name | $R_1$ | $R_2$ |
|---|---|---|---|
| Acecarbromal | (1-acetyl-2-(2-bromo-2-ethylbutyryl)urea | $CH_3CO$ | $(C_2H_5)_2\underset{Br}{C}{-}$ |
| Apronalide | (2-isopropyl-4-pentenoyl)urea | H | $(CH_3)_2CH{-}\underset{CH_2{=}CH{-}CH_2}{CH}{-}$ |
| Bromisovalum | (2-bromo-3-methylbutyryl)urea | H | $(CH_3)_2CH{-}\underset{Br}{CH}{-}$ |
| Capuride | (2-ethyl-3-methylvaleryl)urea | H | $C_2H_5CH{-}\underset{CH_3\ \ \ C_2H_5}{CH}{-}$ |
| Carbromal | (2-bromo-2-ethylbutyryl)urea | H | $(C_2H_5)_2\underset{Br}{C}{-}$ |
| Ectylurea | (2-ethyl-cis-crotonoyl)urea | H | $CH_3CH_2\underset{CH_2CH}{\overset{\|\|}{C}}{-}$ |

Examples of these ureides include those listed above and:
glutethimide (3-ethyl-3-phenyl-piperidine-2,6-dione)
phenytoin (5,5-diphenyl-2,4-imidazolidinedione)
ethosuximide (3-ethyl-3-methyl-2,5-pyrrolidinedione)
5,5-diphenylbarbituric acid
5-phenyl-5-ethylbarbituric acid
5,5-diethylbarbituric acid The preferred family of reactant ureides is the barbituric acids disubstituted at 5, as in structure IV with the R groups preferably being the same or different alkyl or aryl groups, and most preferably with both R groups being phenyl.

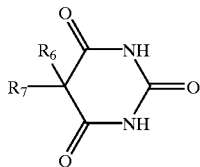

IV

Analogous products resulting from the process of the invention, where 5,5-diphenyl-barbituric acid is a substrate, include:
N,N'-bisethoxymethyl derivative using reagent 2 of Table 1.
N,N'-bismethoxybenzylidene derivative using reagent 7 of Table 1.
N,N'-bismethoxyethylidene derivative using reagent 8 of Table 1.
N,N'-bisbenzyloxymethyl derivative using reagent 3 of Table 1.

The N-methoxymethyl derivative of 5,5-diphenylbarbituric acid (Formula IX) may be prepared by the process of this invention.

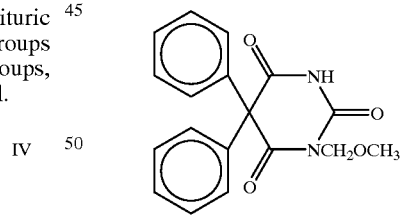

IX

The substrate 5,5-diphenylbarbituric acid is converted to its di-anion salt with a very strong base (as strong as a hydride, e.g. NaH) and then one equivalent is added of the alkoxyalkylating agent, reagent 1 of Table 1. N-methoxymethyl-5,5-diphenylbarbituric acid is obtained by optimizing the reaction to favor monosubstitution. For example, an excess of the very strong base NaH is used, greater than two molar equivalents per mole of the ureide. The monosubstituted product is separated by chromatography or other conventional methods and may be characterized by melting point and nuclear magnetic resonance.

Pharmaceutically-effective salts of the alkylated ureides are also contemplated within the scope of the invention.

In general, stoichiometric amounts of the components are used. That is, for mono-alkylation, the ratio of ureide:alkylating agent:base is about 1:1:2; for di-substitution, the ratio is about 1:2:2, and so on. Different ratios may be appropriate depending on the reaction conditions. A person of ordinary skill will recognize that by varying these ratios, the reaction may proceed faster or slower and have higher or lower yield of end products. For example, as discussed above, mono-substitution of a ureide of the barbituric acid family is favored by using excess base.

For the reaction to proceed a non-aqueous basic catalyst is required. The base may be as strong as sodium hydride or as weak as a tertiary amine. For disubstituted products, the basic catalyst is preferably an amine that does not compete with the substrate ureide (or imide). To this end primary and secondary amine catalysts are excluded. Tertiary amines, which react more slowly with the alkylating species, are preferred to minimize the competing reaction through steric hindrance (branching in the amine substituents). Especially preferred for this attribute are highly hindered amines, such as the readily available amine, ethyl di-isopropyl amine. The hindrance inhibits quarternization of the catalyst amine by the alkylating agent in competition with the ureide substrate, while not interfering significantly with ability of the amine to act as a base (accept a proton). Useful bases include sodium hydride, potassium hydride, lithium hydride, triethylamine, tri-n-propylamine, and di-isopropyl ethyl amine.

The solvent is chosen so as not to compete with the substrate and to maximize the rate of alkylation. The use of dipolar aprotic solvents such as dimethyl formamide, dimethyl sulfoxide, dimethylacetamide, sulfolane, N-methylpyrrolidone, etc., appears to optimize these attributes. Otherwise, any dipolar aprotic solvent may be selected by the person of ordinary skill so long as the solvent is capable of bringing the reactants into solution. The preferred temperature range for the alkylation process is at or near ambient temperature (25±5° C.). Higher temperatures tend to stimulate competitive side-reactions between the alkylating agent and the tertiary amine catalyst (where the latter is being used).

Yields according to the invention are at least as high as with prior art methods. The high yields complement the other advantages of the inventive method including the facts that it is much safer, more convenient, and economical, and allows for ready synthesis of new compounds.

A preferred embodiment of the inventive alkylation process (which employs the preferred substrate and preferred reagent illustrated above) affords the N,N' disubstituted barbituric acid depicted as structure V where the R groups are phenyl.

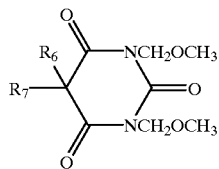

V

N,N'-bismethoxymethyl-5,5-diphenylbarbituric acid

The alkylation preferably takes place in a solvent which is usually a dipolar aprotic solvent like an N,N-dialkylamide. However, other types of aprotic solvents may also be employed, so long as they are compatible with the base. This alkylating technique is particularly novel and convenient in that the active alkylating species may also be generated in situ by employing precursor substances without isolation of the sulfonate reagent itself. Thus, dimethoxymethane (structure VI) may be reacted with the mixed anhydride of acetic and methanesulfonic acids (structure VII) and the resulting in situ generated sulfonate ester, methoxymethyl methanesulfonate (structure VIII, which is structure III where $R_3$=H, $R_4$=H, and $R_5$=$CH_3$) may be applied without isolation or purification to the N-alkylation of the barbituric acid.

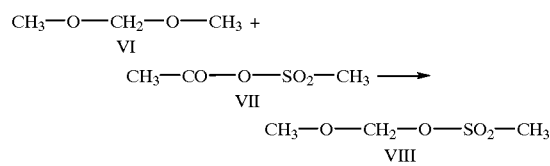

The following examples are intended to illustrate various embodiments of the invention without limiting its scope.

EXAMPLE 1

N,N'-bismethoxymethyl-5,5-diphenylbarbituric acid

A. Using a Hindered Tertiary Amine Catalyst

Dimethoxymethane (10.85 g) was added at 0° C. to 19.7 g of acetylmethanesulfonate. The reaction was stirred at 25° C. for 2 hours. The resultant solution was then added gradually over 45 minutes to a mixture of 10 g of 5,5-diphenylbarbituric acid and 13.85 g of N,N-diisopropyl ethyl amine in 60 ml of dry dimethylformamide. The resultant reaction mixture was stirred for about 15 minutes and then diluted with 180 ml of 2 N HCl, followed by 300 ml of ethyl acetate. The phases were separated and the ethyl acetate phase was washed first with 150 ml of saturated aqueous sodium chloride and then with 150 ml of 2N aqueous NaOH. The organic (ethyl acetate) phase was dried over anhydrous sodium sulfate, filtered and concentrated to dryness to give 12.2 g of N,N'-bismethoxymethyl-5,5-diphenylbarbituric acid. Crystallization from 48 ml of toluene afforded 10.5 g of pure product (79.6% yield).

B. Using Triethylamine as Catalyst

By the procedure of example A, using 10.84 g. of triethylamine (in place of 13.85 g of diisopropylethylamine), there resulted 10.62 g of crude alkylated product. Crystallization from 40 ml of toluene afforded 7.6 g (58.5%) of N,N'-bismethoxymethyl 5,5-diphenylbarbituric acid.

C. Using Sodium Hydride as Catalyst

By the procedure of example A, using 3.57 g of sodium hydride (60% dispersion in mineral oil) in place of the amine catalyst, there resulted after crystallization from toluene 5.0 g (38%) of N,N'-bismethoxymethyl-5,5-diphenylbarbituric acid.

D. Using Acetylbenzenesulfonate in place of acetylmethanesulfonate

By the procedure of example A, using 28.55 g of acetylbenzenesulfonate in place of acetylmethanesulfonate (19.7 g), the pure alkylated product resulted in 75.5% yield.

Completion of the reaction may be checked using conventional methods such as by TLC on silica (mobile phase chloroform methanol 98:2). The reaction mixture is diluted with 360 ml of water and extracted with 480 ml of ethyl acetate. The organic layer is separated and washed twice with 150 ml of water. The solvent is removed by distillation under reduced pressure in order to obtain crude product. The crude product may be purified by crystallization from 4 parts of toluene. The mixture is heated to reflux to disolve and cooled to room temperature. According to HPLC the product of the inventive method has 98–100% purity, and yields of about 60–80% may be expected.

EXAMPLE 2

N,N'-Bisethoxymethyl-5,5-diphenylbarbituric acid

By the procedure of Example 1A, using diethoxymethane (15.42 g) in place of dimethoxymethane (10.85 g), there is obtained a 68% yield of pure N,N'-bisethoxymethyl-5,5-diphenylbarbituric acid.

EXAMPLE 3

3-Methoxymethylphenytoin

By the procedure of 1A, using phenytoin (18 g) in place of 5,5-diphenylbarbituric acid (10 g), there is obtained a 70% yield of 3-methoxymethylphenytoin.

EXAMPLE 4

N-Methoxymethylglutethimide

By the procedure of 1A, using glutethimide (15.5 g) in place of 5,5-diphenylbarbituric acid (10 g) there is obtained a 65% yield of N-methoxymethylglutethimide.

EXAMPLE 5

N-Methoxymethylethosuximide

By the procedure of 1A, using ethosuximide (10 g) in place of 5,5-diphenylbarbituric acid (10 g), there is obtained a 60% yield of N-methoxymethylethosuximide.

EXAMPLE 6

N-Methoxymethyl-5,5-diphenylbarbituric acid

The monosubstituted methoxymethyl derivative is obtained by optimizing the procedure of Example 1A to favor monosubstitution, using an excess of NaH and one equivalent of alkylating agent per equivalent of ureide. The monosubstituted product is separated and characterized.

The compounds of examples 2–6 have advantageous pharmaceutical properties over a sustained period of time. They may be used to treat mammals including humans for convulsions, seizures, muscle stiffness, nervous strain or anxiety, by administering an effective amount of the compound in a pharmaceutically acceptable carrier to the patient.

The embodiments illustrated and discussed in this specification are intended only to teach those skilled in the art the best way known to the inventors to make and use the invention. Nothing in this specification should be considered as limiting the scope of the present invention. Modifications and variations of the above-described embodiments of the invention are possible without departing from the invention, as appreciated by those skilled in the art in light of the above teachings. It is therefore to be understood that, within the scope of the claims and their equivalents, the invention may be practiced otherwise than as specifically described.

What is claimed is:

1. A method of N-alkylating ureides comprising reacting a ureide of formula I

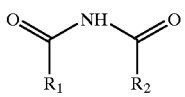

with an ester of a sulfonic acid of formula III

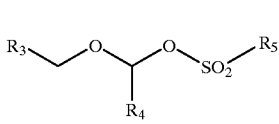

in the presence of a base in an aprotic reaction medium, to provide a corresponding alkylated ureide, wherein $R_1$ and $R_2$ are each either non-cyclic alkyl, aryl, arylalkyl, or $R_1$ and $R_2$ together form a cyclic group having a total of at least 5 atoms each of which is selected from the group consisting of carbon, nitrogen and oxygen, and wherein $R_3$=H, lower alkyl, phenyl, or alkyl substituted phenyl, $R_4$=H, lower alkyl, phenyl, or alkyl substituted phenyl, and $R_5$=lower alkyl, phenyl, or alkyl substituted phenyl.

2. A process for N-alkylation of a ureide comprising: reacting a ureide of formula I

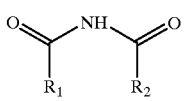

with an ester of a sulfonic acid of Formula III

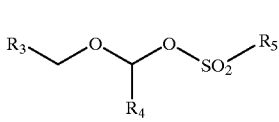

in the presence of a base and an aprotic solvent, wherein one of $R_1$ and $R_2$ is $NH_2$, $NHCOCH_3$, or non-cyclic alkyl, aryl, arylalkyl, or haloalkyl, and the other of $R_1$ and $R_2$ is non-cyclic alkyl, aryl, arylalkyl, or haloalkyl, or wherein $R_1$ and $R_2$ together form a cyclic group selected from the group consisting of $NHCOC(R_6)(R_7)$, $NHC(R_6)(R_7)$, $CH_2CH_2C(R_6)(R_7)$, $OC(R_6)(R_7)$ and $CH_2C(R_6)(R_7)$, wherein $R_6$ and $R_7$, are each either noncyclic alkyl, aryl or arylalkyl, and wherein $R_3$=H, lower alkyl, phenyl, or alkyl substituted phenyl, $R_4$=H, lower alkyl, phenyl, or alkyl substituted phenyl, and $R_5$=lower alkyl, phenyl, or alkyl substituted phenyl, to provide a resultant N-alkoxyalkylated ureide.

3. A process according to claim 2, wherein the ureide is a 5,5-disubstituted barbituric acid.

4. A process according to claim 2, wherein the ureide is 5,5-diphenyl barbituric acid, the ester of a sulfonic acid is selected from the group consisting of methoxymethyl methanesulfonate, methoxymethyl ethanesulfonate, methoxymethyl benzenesulfonate, and methoxymethyl p-toluenesulfonate, the base is di-isopropyl ethyl amine, and the resultant ureide is N,N'-bismethoxymethyl-5,5-diphenyl barbituric acid.

5. A process according to claim 2, wherein the ureide is selected from the group consisting of 5,5-diphenyl barbituric acid, phenytoin, glutethimide, ethosuximide, 5-phenyl-5-ethylbarbituric acid, and 5,5-diethylbarbituric acid.

6. A process according to claim 2, wherein the ureide is selected from the group consisting of acecarbromal, apronalide, bromisolvalum, capuride, carbromal, ectylurea, hydantoins, glutarimides, oxazolidinediones, succinimides, and barbiturates.

7. A process according to claim 2, wherein the ester of a sulfonic acid is methoxymethyl methanesulfonate.

8. A process according to claim 2, wherein the ester of a sulfonic acid is selected from the group consisting of ethoxymethyl methanesulfonate, benzyloxymethyl methanesulfonate, methoxymethyl ethanesulfonate, methoxymethyl benzenesulfonate, methoxymethyl p-toluenesulfonate, methoxylbenzylidene methanesulfonate, and methoxyethylidene methanesulfonate.

9. A process according to claim 2, wherein the base is non-aqueous with a strength between sodium hydride and a tertiary amine.

10. A process according to claim 2, wherein the base is a tertiary amine.

11. A process according to claim 2, wherein the base is selected from the group consisting of sodium hydride, potassium hydride, lithium hydride, triethyl amine, tri-n-propylamine, and di-isopropyl ethyl amine.

12. A process according to claim 2, wherein the ester of a sulfonic acid is produced in situ and is combined directly with the ureide without isolating the ester of a sulfonic acid.

13. A process according to claim 2, further comprising reacting a mixed anhydride of acetic acid and a sulfonic acid with a dialkoxymethane to provide the ester of the sulfonic acid in situ and combined with the ureide without isolating the ester of the sulfonic acid.

14. A process according to claim 2, wherein the ureide is 5,5-disubstituted barbituric acid, which is converted to its di-anion salt with a strong base, and one equivalent of the ester of a sulfonic acid is added, to provide the corresponding mono-alkylated barbituric acid.

15. A process according to claim 2, wherein the aprotic reaction medium is a dipolar solvent.

16. A process according to claim 2, wherein the dipolar solvent is selected from the group consisting of dimethyl formamide, dimethyl sulfoxide, dimethylacetamide, sulfolane, and N-methylpyrrolidone.

17. A process according to claim 3, wherein the the ureide is 5,5-diphenyl barbituric acid, the ester of a sulfonic acid is selected from the group consisting of methoxymethyl methanesulfonate, ethoxymethyl methanesulfonate, benzyloxymethyl methanesulfonate, methoxymethyl ethanesulfonate, methoxymethyl benzenesulfonate, methoxymethyl p-toluenesulfonate, methoxylbenzylidene methanesulfonate, methoxyethylidene methanesulfonate, the base is a non-aqueous base selected from a hydride or an amine, and the process further comprises isolating the resultant alkoxyalkylated 5,5-diphenyl-barbituric acid.

18. A process according to claim 17, wherein the ureide is alkoxyalkylated to an N-mono-alkoxyalkylated 5,5-diphenyl barbituric acid.

19. A process according to claim 18, wherein the ester is a methoxymethyl ester, the base is very strong and is present in excess, and the isolated compound is N-methoxymethyl -5,5-diphenylbarbituric acid.

20. An alkoxyalkylated ureide compound selected from the group consisting of N-methoxymethyl ethosuximide, N-methoxymethyl glutethimide, and N-methoxymethyl-5,5-diphenylbarbituric acid.

21. A compound according to claim 20, wherein the compound is N-methoxymethyl ethosuximide.

22. A compound according to claims 20, wherein the compound is N-methoxymethyl glutethimide.

23. A compound according to claim 20, wherein the compound is N-methoxymethyl-5,5-diphenylbarbituric acid.

24. A method of treating a mammal for a condition selected from the group consisting of convulsions, seizures, muscle stiffness, or anxiety comprising administering to a patient in need of such treatment an effective amount of a pharmaceutical agent comprising a compound according to claim 20.

25. A method of N-alkylating ureides comprising reacting a ureide of formula I

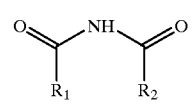

with an ester of a sulfonic acid of formula III

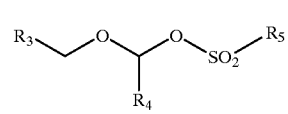

in the presence of a base in an aprotic reaction medium, to provide a corresponding alkylated ureide, wherein $R_1$ and $R_2$ together form a cyclic group having a total of at least 5 atoms each of which is selected from the group consisting of carbon nitrogen and oxygen, and wherein $R_3$=H, lower alkyl, phenyl, or alkyl substituted phenyl, R4=H, lower alkyl, phenyl, or alkyl substituted phenyl, and $R_5$=lower alkyl, phenyl, or alkyl substituted phenyl.

26. A process for N-alkoxyalkylation of a ureide comprising:
reacting a ureide of formula IV

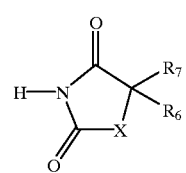

with an ester of a sulfonic acid of Formula III

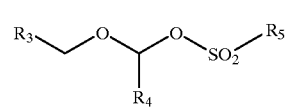

in the presence of a base and an aprotic solvent, wherein X is O, NH, $CH_2$, $CH_2$—$CH_2$ or C(O)NH, and wherein $R_6$ and $R_7$ are each either noncyclic alkyl, aryl or arylalkyl, and wherein $R_3$=H, lower alkyl, phenyl, or alkyl substituted phenyl, $R_4$=H, lower alkyl, phenyl, or alkyl substituted phenyl, and $R_5$=lower alky, phenyl, or alkyl substituted phenyl, to provide a resultant N-alkoxyalkylated ureide.

* * * * *